United States Patent [19]

Massett

[11] Patent Number: 4,698,444

[45] Date of Patent: Oct. 6, 1987

[54] 1,1-BIS(P-FLUOROPHENYL)UREA

[75] Inventor: Stephen S. Massett, Groton, Conn.

[73] Assignee: Pfizer Inc., New York, N.Y.

[21] Appl. No.: 809,959

[22] Filed: Dec. 17, 1985

Related U.S. Application Data

[62] Division of Ser. No. 641,250, Aug. 16, 1984, Pat. No. 4,568,748, which is a division of Ser. No. 425,151, Sep. 30, 1982, Pat. No. 4,477,669.

[51] Int. Cl.$^4$ ............................................. C07C 127/19
[52] U.S. Cl. ......................................... 564/54; 546/85; 546/86; 546/87; 564/310
[58] Field of Search ........................................... 546/54

[56] References Cited

U.S. PATENT DOCUMENTS

| | | | |
|---|---|---|---|
| 4,001,263 | 1/1977 | Plattner et al. | 546/85 |
| 4,014,890 | 3/1977 | Welch | 546/85 |
| 4,224,329 | 9/1980 | Welch | 514/292 |
| 4,267,331 | 5/1981 | Welch | 546/85 |
| 4,568,748 | 2/1986 | Massett | 546/85 |

OTHER PUBLICATIONS

Robinson, Chem. Abstracts, vol. 55, (21), pp. 22,194a–b, Oct. 16, 1961.
Romanova et al., Chem. Abstracts, vol. 72, (7), Abst. No. 31, 403z, Feb. 16, 1970.
Weigert et al., The Journal of Organic Chemistry, vol. 41, (25), pp. 4006–4012 (Dec. 10, 1976).
Harbert et al., J. Med. Chem. 23, pp. 635–643 (1980).
Murakami et al., Heterocycles 12, pp. 1571–1574 (1979).
Rylander, "Catalytic Hydrogenation Over Platinum Metals", Academic Press, 1967, pp. 291–303.

*Primary Examiner*—Alan L. Rotman
*Attorney, Agent, or Firm*—Peter C. Richardson; Albert E. Frost; Robert K. Blackwood

[57] ABSTRACT

1,1-Di(p-fluorophenyl)urea, 2-carbobenzoxy-8-fluoro-5-(p-fluorophenyl)-2,3,4,5-tetrahydro-1H-pyrido[4,3-b]indole, an efficient process for converting the former to the latter, further comprising conversion of the latter to 8-fluoro-5-(p-fluorophenyl)-2-[4-(p-fluorophenyl)-4-hydroxybutyl)]-2,3,4,5-tetrahydro-1H-pyrido[4,3-b]indole (flutroline) or to 8-fluoro-5-(p-fluorophenyl)-2,3,4,5-tetrahydro-1H-pyrido[4,3-b]indole (an alternative flutroline intermediate).

1 Claim, No Drawings

1,1-BIS(P-FLUOROPHENYL)UREA

CROSS-REFERENCE TO RELATED APPLICATIONS

This application is a division of copending application Ser. No. 641,250, filed Aug. 16, 1984, now U.S. Pat. No. 4,568,748, which is a division of application Ser. No. 425,151, filed Sept. 30, 1982, now U.S. Pat. No. 4,477,669.

BACKGROUND OF THE INVENTION

This invention relates to novel intermediates and processes useful in the preparation of 8-fluoro-5-(p-fluorophenyl)-2-[4-(p-fluorophenyl)-4-hydroxybutyl)]-2,3,4,5-tetrahydro-1H-pyrido[4,3-b]indole, also known as flutroline, a neuroleptic agent having valuable therapeutic activity, see Plattner et al., U.S. Pat. No. 4,001,263, and Harbert et al., J. Med. Chem. 23, pp. 635–643.

Plattner et al. and Harbert et al. also describe the earliest synthesis of flutroline: p-Fluorophenylhydrazine is condensed with N-carbethoxy-4-piperidone to form 8-fluoro-2-carbethoxy-2,3,4,5-tetrahydro-1H-pyrido[4,3-b]indole. By the Ullman reaction the latter is arylated to form the 5-(p-fluorophenyl) derivative and then hydrolyzed under vigorous basic conditions to yield 8-fluoro-5-(p-fluorophenyl)-2,3,4,5-tetrahydro-1H-pyrido[4,3-b]indole. The synthesis of flutroline is completed by 2-alkylation with 3-(p-fluorobenzoyl)propyl chloride and finally reduction of the ketone group to an alcohol group.

Welch, U.S. Pat. No. 4,014,890 has described an alternative synthesis of the same earlier intermediate 8-fluoro-5-(p-fluorophenyl)-2-carbethoxy-2,3,4,5-tetrahydro-1H-pyrido[4,3-b]indole, viz., by condensation of 1,1-di(p-fluorophenyl)hydrazine with N-carbethoxy-4-piperidone. In contrast to the present 2-carbobenzoxy intermediate, the earlier 2-carbethoxypyridoindole is a waxy solid difficult to isolate and purify by crystallization. Furthermore, in the further conversion to flutroline, the carbethoxy group must be removed under harsh, basic conditions, producing undesirable by-products which interfere with further processing (particularly by hydrogenation) and render difficult the isolation of flutroline in the highly purified form required for its use in therapy.

Welch, U.S. patent application, Ser. No. 334,195, filed December 24, 1981 has described the preparation of flutroline by the reductive alkylation of 8-fluoro-5-(p-fluorophenyl)-2,3,4,5-tetrahydro-1H-pyrido[4,3-b]indole (derived by the above earlier process) with the lactol, 2-(p-fluorophenyl)-5-hydroxytetrahydrofuran. Surprisingly, under hydrogenation conditions, the present carbobenzoxy derivative is converted more readily (milder conditions and/or more rapidly) to flutroline.

Welch, U.S. Pat. No. 4,267,331 has also described the preparation of related hexahydropyrido-indole by reductive alkylation of 8-fluoro-5-(p-fluorophenyl)-2,3,4,4a,5,9b-hexahydro-1H-pyrido[4,3-b]indole.

Murakami et al., Heterocycles 12, pp. 1571–1574 (1979) have described the preparation of unsymmetrical diarylhydrazines by reaction of aqueous sodium hypochlorite with unsymmetrical diarylureas in ethanol. Such hydrazines were condensed with pyruvate to form N-arylindole derivatives. In the present instance, Murakami's conditions failed to provide the required 1,1-di(p-fluorophenyl)hydrazine.

The present 2,3,4,5-tetrahydro-1H-pyrido[4,3-b]indoles are alternatively named as 1,2,3,4-tetrahydrogamma-carbolines. In either case, the ring system is numbered as follows:

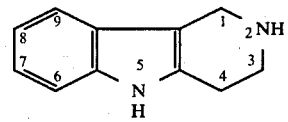

SUMMARY OF THE INVENTION

The present invention embraces a process for preparing 2-carbobenzoxy-8-fluoro-5-(p-fluorophenyl)-2,3,4,5-tetrahydro-1H-pyrido[4,3-b]indole, which comprises the steps of (a) chlorinating 1,1-di(p-fluorophenyl)urea with a chlorinating agent, such as a ($C_1$–$C_4$)alkyl hypochlorite, in a step (a) reaction-inert solvent to form a first intermediate, 3-chloro-1,1-di(p-fluorophenyl)urea, in situ;

(b) rearranging the intermediate 3-chlorourea by the action of an alkali metal ($C_1$–$C_3$)alkoxide in a step (b) reaction-inert solvent to form a second intermediate, 2-($C_1$–$C_3$)carbalkoxy-1,1-di(p-fluorophenyl)hydrazine, in situ;

(c) hydrolyzing and decarboxylating the intermediate carbalkoxyhydrazine with water in the presence of base in a step (c) reaction-inert solvent to form a third intermediate, 1,1-di(p-fluorophenyl)hydrazine, in situ;

(d) condensing the intermediate 1,1-di(p-fluorophenyl)hydrazine with N-carbobenzoxy-4-piperi-done in the presence of a strong acid in a step (d) reaction-inert solvent, and recovering said 2-carbobenzoxy-8-fluoro-5-(p-fluorophenyl)-2,3,4,5-tetrahydro-1H-pyrido[4,3-b]indole.

The preferred ($C_1$–$C_4$)alkyl hypochlorite is t-butyl hypochlorite. The preferred alkali metal alkoxide is sodium methoxide, whereby the second intermediate is specifically 2-carbomethoxy-1,1-(p-diphenyl)hydrazine. The preferred strong acid is a mineral acid. Most preferred is hydrochloric acid.

The above process further comprises hydrogenation of said 2-carbobenzoxy-8-fluoro-5-(p-fluorophenyl)-2,3,4,5-tetrahydro-1H-pyrido[4,3-b]indole over a noble metal catalyst to form 8-fluoro-5-(p-fluorophenyl)-2,3,4,5-tetrahydro-1H-pyrido[4,3-b]indole (an alternative intermediate also useful in the preparation of flutroline); or a similar such hydrogenation but in the presence of substantially one molar equivalent of a lactol, 2-(p-fluorophenyl)-5-hydroxytetrahydrofuran, to form flutroline. In either case, the preferred noble metal is palladium and the preferred hydrogen pressure is 2–8 atmospheres.

Also embraced by the present invention is the separate process step for the conversion of 8-fluoro-5-(p-fluorophenyl)-2-carbobenzoxy-2,3,4,5-tetrahydro-1H-pyrido[4,3-b]indole to flutroline per se, as delineated above; and the present novel and valuable flutroline intermediates 1,1-di(p-fluorophenyl)urea and 2-carbobenzoxy-8-fluoro-5-(p-fluorophenyl)-2,3,4,5-tetrahydro-1H-pyrido[4,3-b]indole.

As used herein, the expression "reaction-inert solvent" refers to a solvent which does not interact with reagents, intermediates or products in such a manner as to adversely affect conversion to the desired intermediate, or the yield or quality of the desired product. In all cases, suitable reaction-inert solvents are disclosed and exemplified below.

DETAILED DESCRIPTION OF THE INVENTION

The present flutroline intermediate, 2-carbobenzoxy-8-fluoro-5-(p-fluorophenyl)-2,3,4,5-tetrahydro-1H-pyrido[4,3-b]indole is prepared by the four steps, (a) to (d), which are defined above. The various step intermediates can be isolated, if desired. However, it is one of the features of the present highly efficient process to simply employ these intermediates in situ, avoiding the time consuming isolation and the inevitable loss of these valuable intermediates, while at the same time attaining the above flutroline intermediate in a high state of purity, suitable for further processing (particularly processing which involves hydrogenation) and ultimately yielding flutroline in the high state of a purity required for its use in therapy.

Step (a) of the present process, chlorination of 1,1-di(p-fluorophenyl)urea, can be carried out by the action of substantially one equivalent of a ($C_1$–$C_4$)-alkyl hypochlorite or a similar chlorinating agent. For reasons of mutual solubility in a common solvent, an alkyl hypochlorite is preferred; for reasons of ready availability and solubility properties, t-butyl hypochlorite is most preferred. Lower temperatures are generally used for the chlorination step, e.g., −10 to 10° C., conveniently 0–5° C. obtained by an icewater bath. The preferred reaction-inert solvents are water-misible, readily dissolve both reactants, and are suitable for the further steps (b) to (d). Especially well-suited are ($C_1$–$C_3$)alkanols, particularly methanol.

Step (b) involves rearrangement with loss of the elements of HCl and gain of the elements of ($C_1$–$C_3$)-alkanol to form the intermediate carbalkoxy hydrazine. This step is readily accomplished by simple addition of substantially two equivalents of an alkali metal ($C_1$–$C_3$)alkoxide, conveniently sodium methoxide, maintaining the same reaction inert-solvent as used in step (a). The alkoxide is conveniently added at the temperature used for step (a). Step (b) proceeds readily at moderate temperatures, e.g., 0–50° C., and is conveniently carried out at ambient temperatures, usually in the range of about 17–27° C.

Step (c), which involves base catalyzed hydrolysis and decarboxylation, is readily accomplished by simply adding excess water to the reaction mixture, otherwise maintaining the same reaction-inert solvent as used in steps (a) and (b). Step (c) occurs most readily at somewhat higher temperature than steps (a) and (b), e.g., 50°–100° C., preferably about 60–75° C. When the solvent boils below the desired reaction temperature, the solvent is partially removed by distillation, optionally with the addition of more water. Alternatively, the reaction is carried out under pressure.

Step (d), formation of the desired carbobenzoxy-pyridoindole from the step (c) hydrazine and N-carbobenzoxy-4-piperidone involves initial formation of a hydrazone, which is followed by cyclization. If desired, the initial phase is accomplished simply by adding the piperidine and excess of a ($C_1$–$C_4$)alkanoic acid, preferably and conveniently acetic acid, to the hydrazine product of step (c), and warming to about 60°–110° C., conveniently to reflux (about 65° to 100° C., depending upon the exact composition of solvents in the reaction mixture). Cyclization is then accomplished by adding an excess of a strong acid, preferably a strong mineral acid such as conc. hydrochloric acid, followed by further heating in the same elevated temperature range. Alternatively and preferably, both hydrazone formation and cyclization are accomplished by heating in the strong acid, omitting the separate step in weak acid. The intermediate product, 2-carbobenzoxy-8-fluoro-5-(p-fluorophenyl)-2,3,4,5-tetrahydro-1H-pyrido[4,3-b]indole, is readily recovered by standard methods of solvent displacement, extraction, concentration and crystallization.

Generally, the above intermediate product is further processed by a hydrogenation step, either hydrogenation to 8-fluoro-5-(p-fluorophenyl)-2,3,4,5-tetrahydro-1H-pyrido[4,3-b] indole (which can then be converted to flutroline by one of a number of methods, e.g., see references cited above), or hydrogenation in the presence of substantially one equivalent of the lactol, 2-(p-fluorophenyl)-5-hydroxytetrahydrofuran, producing flutroline.

In either case, the hydrogenation is carried out in a reaction-inert solvent, under a hydrogen atomsphere, in the presence of a hydrogenation catalyst such as nickel, or a noble metal. Such catalysts are used in an amount sufficient to catalyze the process. As is well known in the art of catalytic hydrogenation, the amount of catalyst required will vary with the nature of the catalyst, the activity of a particular batch of catalyst and the exact conditions of the hydrogenation (e.g., the reactor, the type and amount of agitation, temperature, pressure, solvent). While the amount of catalyst will be generally similar to the amounts which are illustrated in the examples below, routine experimentation will define optimal amounts in specific cases.

The noble metal catalysts as employed in the present invention include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be preformed or formed in situ by reduction of an appropriate salt of the catalytic compound. Examples of preferred catalysts are 5% palladium-on-carbon, 5% platinum-on-carbon, 5% rhodium-on-carbon, platinum chloride, palladium chloride, platinum oxide and ruthenium oxide. The most highly preferred catalyst for reasons of economy and efficiency, is palladium, particularly palladium supported on carbon.

The pressure of the present hydrogenation is not critical and can range from subatmospheric to 100 atmospheres, or higher. Moderate pressures of about 2–8 atmospheres are preferred, since the hydrogenation generally proceeds at a reasonable rate at these pressures and the elaborate and expensive equipment required for higher pressure hydrogenation is avoided.

The temperature of the hydrogenation is also not critical. Temperatures ranging from 0°–75° C. are generally satisfactory. As a matter of convenience, ambient temperatures (about 17°–27° C.) are usually preferred, the cost of cooling or heating thus being avoided.

For the present hydrogenation processes, examples of suitable solvents are ($C_1$–$C_3$)alkyl acetates; ($C_1$–$C_4$) alkanols; ethers such as dimethoxyethane, tetrahydrofuran, dioxane; or isopropyl ether; glycol or glycol monoethers such as 2-methoxyethanol; hydrocarbons such as benzene, toluene and xylene; halocarbons such as methylene chloride or chloroform; water; or combinations of two or more of these solvents. The preferred solvent is either ethyl acetate, or a mixture of ethyl acetate and a ($C_1$-$C_3$) alkanol.

Flutroline (per se or as a pharmaceutically-acceptable salt thereof), as well as the present alternative flutroline intermediate also derived by hydrogenation, are recovered by standard methods of solvent displacement, extraction, concentration and crystallization which are well known in the art.

The required 1,1-di(p-fluorophenyl)urea is conveniently prepared from di(p-fluorophenyl)amine by the action of sodium cyanate in the presence of trifluoroacetic acid, following the method of Murakami (supra). The di(p-fluorophenyl)amine is conveniently prepared by an improved Ullman method, see J. Org. Chem. 26, p. 2721 (1961). The required N-carbobenzoxy-4-piperidone is readily available by reaction of carbobenzoxy chloride with 4-piperidone under conditions well known in the art, or from N-benzyl-4-piperidone as specifically described below. Finally, preparation of the requisite lactol is according to methods disclosed in U.S. Pat. No. 4,267,331 (supra).

The following examples are provided solely for the purpose of illustration and are not to be construed as limitations of the invention, many variations of which are possible without departing from the spirit or scope thereof.

EXAMPLE 1

1,1-Di(p-fluorophenyl)urea

Di(p-fluorophenyl)amine (102.5 g., 0.5 mole) and NaOCN (65 g, 1.0 mole) were stirred in 700 ml $CH_2Cl_2$ at 16° C. $F_3CCOOH$ (84.5 ml, 117 g, 1.025 mole) was added as a thin stream over 5 minutes, during which the reaction mixture exothermed to 28° C. The exotherm peaked at 32° C. shortly after addition was complete. The reaction mixture was stirred at 23°-25° for 21 hours, diluted with 350 ml $H_2O$ and stirred 0.5 hour. The organic layer was separated and stirred 0.25 hour with 40 g NaOH in 500 ml $H_2O$. The layers were separated, and the aqueous layer back washed with 100 ml $CH_2Cl_2$. The combined organic layer and back wash was dried (MgSO$_4$), concentrated to 600 ml, diluted with 600 ml isopropanol, reconcentrated to 600 ml, rediluted with 600 ml of fresh isopropanol, reconcentrated to 800 ml, rediluted with 400 ml fresh isopropanol and again reconcentrated to 800 ml. The mixture was cooled to room temperature (product began to crystallize) and then to 0°-5° C. Title product was recovered by filtration, 104.9 g, m.p. 150°-153° C.

EXAMPLE 2

Step (a). 1,1-Di(p-fluorophenyl)-3-chlorourea t-Butyl hypochlorite (7.5 g, 0.070 mole) was added to 1,1-di(p-fluorophenyl)urea (17.5 g, 0.071 mole) in 440 ml methanol at 0°-5° and the mixture stirred for 1 hour at that temperature to produce a solution containing step (a) title product.

Step (b).
1,1-Di(p-fluorophenyl)-2-carbomethoxyhydrazine

At 0°-5° C., sodium methoxide (7.55 g, 0.14 mole) in 100 ml of methanol was added to the solution of step (a) product. The mixture was stirred 0.5 hour at 0°-5° C. and 2 hours at ambient temperature to yield a solution of step (b) title product.

Step (c). 1,1-Di(p-fluorophenyl)hydrazine

Water (100 ml) was added to the solution of step (b) product and methanol removed by distillation until the pot temperature was 74° C. The mixture was then refluxed 16 hours and finally cooled to ambient temperature to yield a solution of step (c) title product.

Step (d).
8-Fluoro-5-(p-fluorophenyl)-2-carbobenzoxy-2,3,4,5-tetrahydro-1H-pyrido-[4,3-b]indole The solution from step (c) was diluted with 35 ml acetic acid and 16.2 grams (0.0695 mole) of N-carbobenzoxy-4-piperidone was added. The reaction mixture was heated to reflux for 30 minutes, cooled to ambient temperature, acidified with 60 ml conc. HCl, and refluxed an additional 1.5 hours. After adding 100 ml of water, the solution was refluxed for 5 minutes and filtered hot. The solids were washed with water at 45° C., followed by 50 ml of cold methanol, and then dissolved in 400 ml $CH_2Cl_2$. The resulting solution was dried (MgSO$_4$), treated with activated charcoal and filtered. By repeated addition of methanol and distillation to a final pot temperature of 65° C. and a final volume of 200 ml, $CH_2Cl_2$ was displaced with methanol. The resulting slurry of step (d) title product was recovered by filtration, 17.8 g, m.p. 157°-160° C.

Anal. Calcd for $C_{25}H_{20}N_2O_2F_2$: C, 71.76; H, 4.82; N, 6.70; m/e 418. Found: C, 71.76; H, 4.91; N, 6.69; m/e 418.

EXAMPLE 3

Step (a). 1,1-Di(p-fluorophenyl)-3-chlorourea t-Butyl hypochlorite (22.8 g, 0.21 mole) was added to 1,1-di(p-fluorophenyl)urea (49.4 g, 0.2 mole) in 750 ml methanol at 0°-5° and the mixture stirred for 0.5 hour to produce a thin slurry containing step (a) title product.

Step (b).
1,1-Di(p-fluorophenyl)-2-carbomethoxy-hydrazine

At 0°-5° C., sodium methoxide (22.7 g) in 250 ml methanol was added in a thin stream over 5 minutes to the step (a) product mixture. The reaction mixture was warmed to 40°-45° C. for 15 minutes to produce a milky solution of step (b) title product.

Step (c). 1,1-Di(p-fluorophenyl)hydrazine

NaOH (40 g) in 175 ml $H_2O$ was added to the step (b) product mixture. The mixture was distilled at ambient pressure to remove the methanol and the aqueous residue refluxed for 25 hours and cooled to ambient temperature to yield a solution of step (c) title product.

Step (d).
8-Fluoro-5-(p-fluorophenyl)-2-carbobenzoxy-2,3,4,5-tetrahydro-1H-pyrido[4,3-b]indole The solution from step (c) was diluted with 300 ml conc. HCl, maintaining 35° C. or less. N-Carbobenzoxy-4-piperidone (46.6 g, 0.2 mole) was added and the mixture heated to reflux for 1 hour. The resulting thick slurry was filtered hot with water and methanol wash, 64.6 g. The solids were taken into 400 ml CHCl$_2$, carbon treated, dried (MgSO$_4$), and the $CH_2Cl_2$ displaced with methanol to a final volume of 500 ml and purified step (d) title product recovered by filtration, 60.9 g, identical with title product of Example 2.

EXAMPLE 4

8-Fluoro-5-(p-fluorophenyl)-2-[4-(p-fluorophenyl)-4-hydroxybutyl]-2,3,4,5-tetrahydro-1H-pyrido[4,3-b]indole (Flutroline)

In a Parr bottle were combined 5% Pd/C (5 g of 50% water-wet), 8-fluoro-5-(p-fluorophenyl)-2-carbobenzoxy-2,3,4,5-tetrahydro-1H-pyrido[4,3-b]indole (5.0 g, 0.0119 mole) in 100 ml ethyl acetate, and 5.5 grams (0.03 mole) 5-(p-fluorophenyl)-2-hydroxytetrahydrofuran in 100 ml ethyl acetate. The mixture was agitated and hydrogenated at 30–40 psig for 20 hours. The solution was filtered to recover catalyst, with ethyl acetate and $CH_2Cl_2$ wash. The filtrate and washes were concentrated in vacuo to a viscous oil. The oil was dissolved in 400 ml ethyl acetate and filtered. The solution was concentrated to an oil, diluted with 150 ml ether, and filtered to yield title product, 3.8 gm, m.p. 145°–149° C.

EXAMPLE 5

8-Fluoro-5-(p-fluorophenyl)-2,3,4,5-tetrahydro-1H-pyrido[4,3-b]indole

In a Parr bottle were combined 5% Pd/C (10 g of 50% water-wet) and 60 g of 8-fluoro-5-(p-fluorophenyl)-2-carbobenzoxy-2,3,4,5-tetrahydro-1H-pyrido[4,3-b]-indole (60 g, 0.143 mole) in 400 ml ethyl acetate and 100 ml methanol and the mixture hydrogenated at 44–80 psig for 4 hours. Catalyst was recovered by filtration and the filtrate evaporated to solids in vacuo. The residue taken into $CH_2Cl_2$, carbon treated, dried ($Na_2SO_4$) and $CH_2Cl_2$ displaced with hexane by distillation to a final pot temperature of 70° C. The white, crystalline product was recovered by filtration, 35.6 g, m.p. 126°–129° C.

PREPARATION 1

N-Carbobenzoxy-4-piperidone

N-Benzyl-4-piperidone (122.2 g, 0.645 mole) in 500 ml toluene was warmed to 45° C. Benzyl chloroformate (130 ml, 155 g, 0.915 mole) was added in a thin, steady stream, and the reaction mixture heated to reflux for 2 hours, cooled to ambient temperature, diluted with 250 ml $H_2O$ and stirred vigorously 0.5 hour. The organic layer was separated, washed 1×400 ml 6N HCl and then 1×100 ml saturated NaCl, dried ($MgSO_4$), treated with activated carbon, and concentrated to an oil. The oil was distributed between 400 ml ethyl acetate and 400 ml of $H_2O$ containing 67.0 g $NaHSO_3$, stirred 0.5 hour, and the aqueous layer separated, washed with 3 portions of ether, made basic with aqueous NaOH and extracted with fresh ether. The ether layer was dried and reevaporated to yield purified title product as an oil, 136.1 g.

I claim:

1. 1,1-Di(p-fluorophenyl)urea.

* * * * *